US010234528B2

(12) United States Patent
Dale et al.

(10) Patent No.: US 10,234,528 B2
(45) Date of Patent: Mar. 19, 2019

(54) METHOD AND APPARATUS TO CORRECT NOISE EFFECTS IN QUANTITATIVE TECHNIQUES IN MAGNETIC RESONANCE IMAGING

(71) Applicant: SIEMENS AKTIENGESELLSCHAFT, Munich (DE)

(72) Inventors: Brian Dale, Morrisville, NC (US); Stephan Kannengiesser, Wuppertal (DE); Berthold Kiefer, Erlangen (DE); Marcel Dominik Nickel, Herzogenaurach (DE); Xiaodong Zhong, Marietta, GA (US)

(73) Assignee: Siemens Aktiengesellschaft, Munich (DE)

( * ) Notice: Subject to any disclaimer, the term of this patent is extended or adjusted under 35 U.S.C. 154(b) by 552 days.

(21) Appl. No.: 14/858,053

(22) Filed: Sep. 18, 2015

(65) Prior Publication Data

US 2016/0084929 A1   Mar. 24, 2016

Related U.S. Application Data

(60) Provisional application No. 62/052,035, filed on Sep. 18, 2014.

(51) Int. Cl.
*G01R 33/56* (2006.01)
*A61B 5/00* (2006.01)
(Continued)

(52) U.S. Cl.
CPC .......... *G01R 33/5608* (2013.01); *A61B 5/055* (2013.01); *A61B 5/7203* (2013.01); *G01R 33/56341* (2013.01)

(58) Field of Classification Search
CPC .......... G01R 33/5608; G01R 33/56341; A61B 5/055; A61B 5/7203
See application file for complete search history.

(56) References Cited

U.S. PATENT DOCUMENTS

| 8,643,363 | B2* | 2/2014 | Warntjes | ................ | G01R 33/56 |
| | | | | | 324/307 |
| 2011/0018537 | A1* | 1/2011 | Warntjes | ............ | G01R 33/5602 |
| | | | | | 324/309 |

(Continued)

OTHER PUBLICATIONS

Le Bihan et al., "Separation of Diffusion and Perfusion in Intravoxel Incoherent Motion MR Imaging," Radiology, vol. 168, pp. 497-505 (1988).

(Continued)

*Primary Examiner* — G. M. A Hyder
(74) *Attorney, Agent, or Firm* — Schiff Hardin LLP

(57) ABSTRACT

In a method to correct noise effects in magnetic resonance (MR) images, which is executed in a processor (computer), the processor executes a fitting algorithm in order to calculate initial values for each of selected variables in signal model that models noise effects in a modeled, noise-containing MR image. The processor then iteratively executes the same or a different fitting algorithm, in order to generate final values for each of the selected variables. The processor is provided with an actual, acquired MR image that contains noise, and the processor uses the final values of the selected variables to calculate synthetic signal intensities in the MR image, thereby producing a synthetic MR image with no noise bias effects of errors. This synthetic image is made available in electronic form at an output of the processor, as a data file.

17 Claims, 3 Drawing Sheets

(51) Int. Cl.
*A61B 5/055* (2006.01)
*G01R 33/563* (2006.01)

(56) References Cited

U.S. PATENT DOCUMENTS

2014/0126795 A1 5/2014 Zhong et al.
2016/0282433 A1* 9/2016 Kannengiesser .. G01R 33/4828

OTHER PUBLICATIONS

Warach et al., "Acute Human Stroke Studied by Whole Brain Echo Planar Diffusion-weighted Magnetic Resonance Imaging," Ann Neurol, vol. 37, pp. 231-241 (1995).
Walker-Samuel et al., "Robust Estimation of the Apparent Diffusion Coefficient (ADC) in Heterogeneous Solid Tumors," Magnetic Resonance in Medicine, vol. 62, pp. 420-429 (2009).
Kellman et al., "Image Reconstruction in SNR Units: A General Method for SNR Measurement," Magn. Reson. Med., vol. 54, pp. 1439-1447 (2005).
Taylor et al., "The spatial mapping of translational diffusion coefficients by the NMR imaging technique," Phys. Med. Biol., vol. 30, No. 4, pp. 345-349 (1985).
Levenberg et al., "A method for the solution of certain non-linear problems in least squares," Quarterly of applied mathematics, vol. 11, No. 1 (1944).
Veraart et al., "Comprehensive Framework for Accurate Diffusion MRI Parameter Estimation," Magn. Reson. Med., vol. 70, pp. 972-984 (2013).
Aja-Fernández et al., "Noise estimation in single- and multiple-coil magnetic resonance data based on statistical models," Magnetic Resonance Imaging, vol. 27, pp. 1397-1409 (2009).
Le Bihan, "Looking Into the Functional Architecture of the Brain With Diffusion MRI," Nat Rev Neurosci, vol. 4, pp. 469-480 (2003).
Merboldt et al., "Self-Diffusion NMR Imaging Using Stimulated Echoes," Journal of Magnetic Resonance, vol. 64, pp. 479-486 (1985).
Schaefer et al., "Diffusion-weighted MR Imaging of the Brain," Radiology, vol. 217, pp. 331-345 (2000).
Le Bihan et al., "MR Imaging of Intravoxel Incoherent Motions: Application to Diffusion and Perfusion in Neurologic Disorders," Radiology, vol. 161, pp. 401-407 (1986).
Riffe et al., "SNR Estimation in Fast Dynamic Imaging Using Bootstrapped Statistics," Proc, Intl. Soc. Mag. Reson. Med., vol. 15, p. 1879 (2007).
Le Bihan et al., "Imagerie de diffusion in vivo par résonance magnétique nucléaire," C. R. Acad. Sc. Paris, vol. 301, Série II, No. 15, pp. 1109-1112 (1985).
Kristoffersen, "Optimal estimation of the diffusion coefficient from non-averaged and averaged noisy magnitude data," Journal of Magnetic Resonance, vol. 187, pp. 293-305 (2007).
Robson et al., "Comprehensive Quantification of Signal-to-Noise Ratio and g-Factor for Image-Based and k-Space-Based Parallel Imaging Reconstructions," Magn. Reson. Med., vol. 60, No. 4, pp. 895-907 (2008).
Le Bihan et al., "Diffusion Tensor Imaging: Concepts and Applications," Journal of Magnetic Resonance Imaging, vol. 13, pp. 534-546 (2001).
Wiens et al., "Computationally Rapid Method of Estimating Signal-To-Noise Ratio for Phased Array Image Reconstructions," Magnetic Resonance in Medicine, vol. 66, pp. 1192-1197 (2011).
Constantinides et al., "Signal-to-Noise Measurements in Magnitude Images from NMR Phased Arrays," Magn. Reson. Med., vol. 38, pp. 852-857 (1997).
Warach et al., "Fast magnetic resonance diffusion-weighted imaging of acute human stroke," Neurology, vol. 42, pp. 1717-1723 (1992).
Zhong et al., "Liver Fat Quantification Using a Multi-Step Adaptive Fitting Approach with Multi-Echo GRE Imaging," Mag. Reson. Med. (2013).

* cited by examiner

METHOD AND APPARATUS TO CORRECT NOISE EFFECTS IN QUANTITATIVE TECHNIQUES IN MAGNETIC RESONANCE IMAGING

RELATED APPLICATION

The present application claims the benefit of the filing date of Provisional Application No. 62/052,035, filed on Sep. 18, 2014, the contents of which are incorporated herein by reference.

BACKGROUND OF THE INVENTION

Field of the Invention

The present invention concerns methods and apparatuses for magnetic resonance imaging, and in particular concerns a method for reliable parameter estimation from acquired magnetic resonance images with low signal-to-noise ratio (SNR). The reliable parameter estimation can then be used to generate synthetic images using the signal model, which has reduced noise compared to the actual images that are actually acquired, and can be beneficial to appreciate compare to the actual images that are acquired or need to be acquired.

Description of the Prior Art

Magnetic resonance imaging (MRI) is a versatile modality which allows not only qualitative organ or tissue anatomical evaluation but also quantitative assessment of tissue characteristics.

Diffusion MRI, including diffusion weighted imaging (DWI) and diffusion tensor imaging (DTI), is an evolutionary advance in the MRI history (Le Bihan D, Breton E. Imagerie de diffusion in-vivo par résonance magnétique nucléaire. Comptes-Rendus de l'Académie des Sciences 1985; 93:27-34, and Le Bihan D, Breton E, Lallemand D, Grenier P, Cabanis E, Laval-Jeantet M. MR imaging of intravoxel incoherent motions: application to diffusion and perfusion in neurologic disorders. Radiology 1986; 161:401-407, and Merboldt K D, Hanicke W, Frahm J. Self-diffusion NMR imaging using stimulated echoes. J Magn Reson 1985; 64:479-486, and Taylor D G, Bushell M C. The spatial mapping of translational diffusion coefficients by the NMR imaging technique. Phys Med Biol 1985; 30:345-349, and Le Bihan D. Looking into the functional architecture of the brain with diffusion MRI. Nat Rev Neurosci 2003; 4:469-480, and Le Bihan D, Mangin J F, Poupon C, Clark C A, Pappata S, Molko N, Chabriat H. Diffusion tensor imaging: concepts and applications. J Magn Reson Imaging 2001; 13:534-546.). Based on the Brownian motion of water molecules, it provides unique contrasts and characterization between tissues at a cellular level in vivo and non-invasively. Because the diffusion rate of water molecules in different tissues correlates with their physiological state, and can be altered in diseases, DWI has a very important role in clinical applications. As the earliest and most established application, DWI is widely used to diagnose acute ischemic stroke in the brain (Warach S, Chien D, Li W, Ronthal M, Edelman R R. Fast magnetic resonance diffusion-weighted imaging of acute human stroke. Neurology 1992; 42:1717-1723, and Warach S, Gaa J, Siewert B, Wielopolski P, Edelman R R. Acute human stroke studied by whole brain echo planar diffusion-weighted magnetic resonance imaging. Ann Neurol 1995; 37:231-241, and Schaefer P W, Grant P E, Gonzalez R G. Diffusion-weighted MR imaging of the brain. Radiology 2000; 217:331-345).

In DW images, the intensity of each pixel reflects the estimate of the water diffusion rate at that pixel, and is attenuated according to the diffusion weighting (b-value) and direction of the diffusion gradients, as well as on the tissue structure in which the water molecules diffuse. The DW image intensity is known to be described by the Intra Voxel Incoherent Motion (IVIM) model, where both the pure molecular-based diffusion process and the perfusion-based diffusion process related with the incoherent microcirculation contribute to the signal attenuation (Le Bihan D, Breton E, Lallemand D, Aubin M L, Vignaud J, Laval-Jeantet M. Separation of diffusion and perfusion in intravoxel incoherent motion MR imaging. Radiology 1988; 168:497-505). In practice, if two or more DW images with different b-values are acquired, a so-called apparent diffusion coefficient (ADC) map can be calculated, as a single "pure" coefficient to describe the different mechanisms in the diffusion process in a simplified manner. The ADC corresponds to the exponential coefficient in the signal model describing signal loss with increasing b value. Unlike the individual DW images, the ADC map is insensitive to the influence of T1 and T2/T2* effects, provides pixel-by-pixel ADC quantities as a property of the tissue, and therefore is regarded as a quantitative measure of the diffusion. In addition, averaging ADC maps from three orthogonal orientations results in an overall $ADC_{trace}$ map, which further removes diffusion orientation-dependence.

The signal-to-noise ratio (SNR) is relatively low in the DW images, because of the T2* effect and the diffusion weighting. The low SNR poses a challenge for ADC quantification, because the signal of high b-value DW images may drop below the noise floor. In practice, high b-values often have to be used and low SNR cannot be avoided. In addition, some organs such as liver typically have lower SNR on high b-value DW images than the other body regions. The noise in the high b-value images, if not corrected, can cause errors in the resultant ADC map.

SUMMARY OF THE INVENTION

The present invention concerns an approach to account for the noise in the images with low SNR during parameter estimation. This approach can be directly applied to the diffusion imaging to calculate the ADC map, and can be applied to other quantitative MR imaging/mapping techniques for parameter estimation (linear or non-linear) where some source data are contaminated by noise of non-zero expectation value.

The above object is achieved in accordance with the present invention by a method to account for noise effects in quantitative magnetic resonance (MR) image, which is executed in a processor (computer). In accordance with the inventive method, the processor executes an initial fitting algorithm in order to calculate initial values for each of selected variables in signal model that models noise effects in a modeled, noise-containing MR image. The processor then iteratively executes the same or a different fitting algorithm that accounts for the noise effects, in order to generate final values for each of the selected variables. The processor is provided with an actual, acquired MR image that contains noise, and eventually the processor calculates the final values of the selected variables to account for the noise in the actual MR image, thereby producing an accurate estimation of the quantitative measure that is made available in electronic form at an output of the processor, as a data file.

In an embodiment, one of the selected variables is the ADC, and the acquired MR image is a diffusion-weighted MR image, and the final ADC value is calculated with the noise effect corrected.

In a version of this embodiment, the processor uses the ADC to correct the noise effect of the diffusion-weighted MR image when generating an ADC map, which is then applied pixel-by-pixel to the diffusion-weighted MR image.

The method in accordance with the invention can also be used to generate a proton density fat fraction (PDFF) map for fat quantification in an MR image produced by gradient echo imaging, spin echo imaging, or turbo spin echo imaging.

The method can also be employed to generate any of a T2 map, a T2* map, an R2 map or an R2* map for iron quantification in an MR image produced by gradient echo imaging, spin echo imaging or turbo spin echo imaging.

The method according to the invention can also be used to generate a T1 map in inversion recovery imaging or saturation recovery imaging.

One common way to compensate the noise in high b-value diffusion weighted images when calculating the ADC maps is to acquire multiple measurements of diffusion weighted MR images for each high b-value, perform averaging of these multiple measurements for each b-value, and then perform fitting using the averaged b-value images. This averaging approach changes the inherent noise distribution in the diffusion weighted images before and after averaging, and leads to errors in the resultant ADC values and maps. With an embodiment of this invention, it is possible to treat each of those multiple measurements independently in the iterative fitting algorithm, without averaging of those diffusion-weighted images for each b-value. Therefore, the noise distribution is not changed in each measurement of the diffusion-weighted images and in the fitting, therefore the resultant ADC values and maps are more accurate.

The present invention also concerns a magnetic resonance apparatus that is configured to execute any or all embodiments of the method according to the invention as described above.

The present invention also encompasses a non-transitory, computer-readable data storage medium encoded with programming instructions that, when the storage medium is loaded into a processor or a computer, cause the processor or computer to execute any or all embodiments of the method according to the invention, as described above.

DESCRIPTION OF THE PREFERRED EMBODIMENTS

Figure 1:
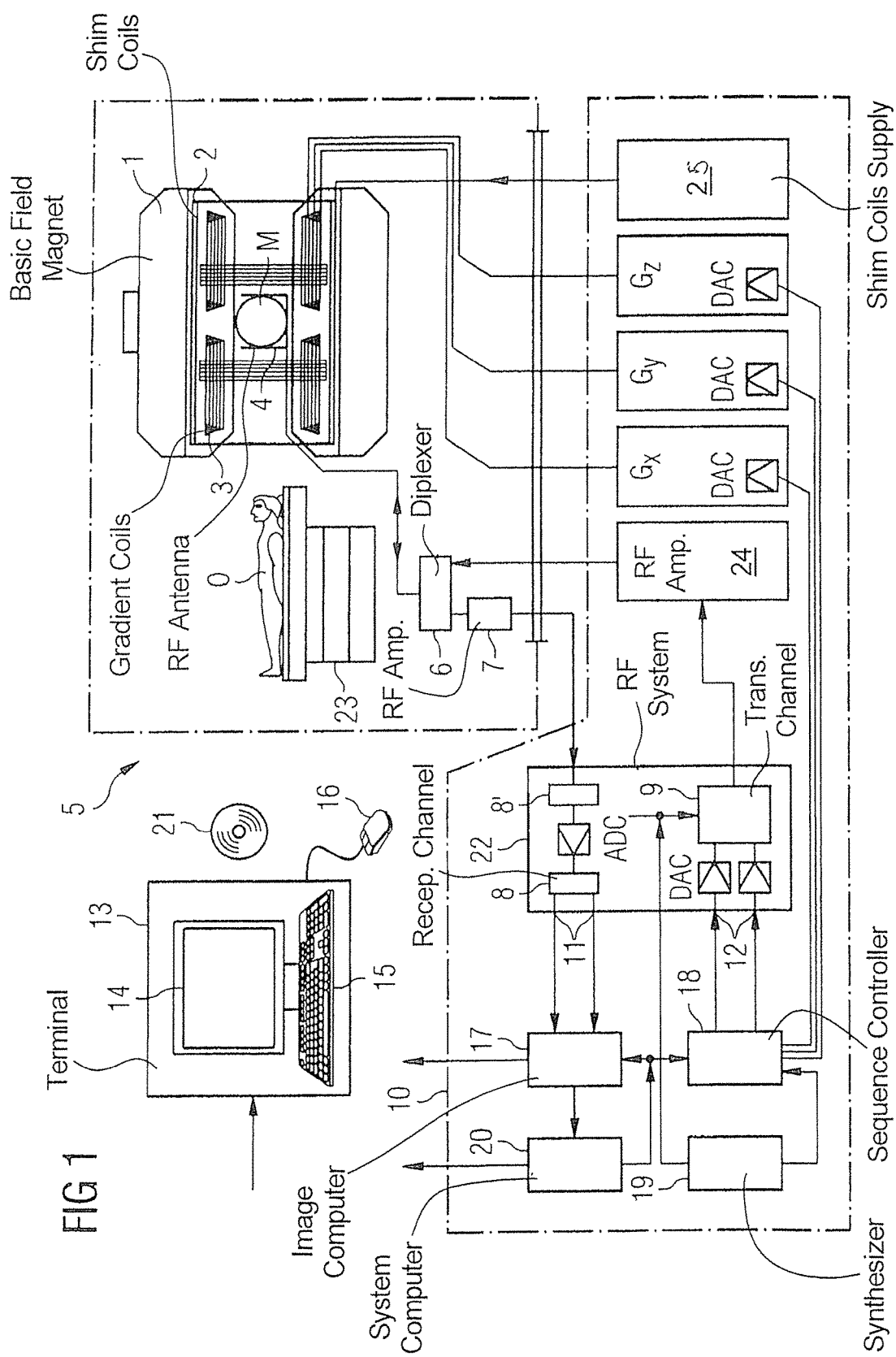
FIG. 1 schematically illustrates a magnetic resonance imaging apparatus that can be configured to execute the method according to the invention.

FIG. 1 schematically illustrates a magnetic resonance apparatus 5 (a magnetic resonance imaging or tomography device). A basic field magnet 1 generates, a temporally constant strong magnetic field for the polarization or alignment of the nuclear spin in a region of an examination subject O, such as a portion of a human body that is to be examined, lying on a table 23 in order to be moved into the magnetic resonance apparatus 5. The high degree of homogeneity in the basic magnetic field necessary for the magnetic resonance measurement (data acquisition) is defined in a typically sphere-shaped measurement volume M, in which the portion of the human body that is to be examined is placed. In order to support the homogeneity requirements temporally constant effects are eliminated by shim-plates made of ferromagnetic materials are placed at appropriate positions. Temporally variable effects are eliminated by shim-coils 2 and an appropriate control unit 25 for the shim-coils 2.

A cylindrically shaped gradient coil system 3 is incorporated in the basic field magnets 1, composed of three windings. Each winding is supplied by a corresponding amplifier with power for generating a linear gradient field in a respective axis of a Cartesian coordinate system. The first partial winding of the gradient field system 3 generates a gradient $G_x$ in the x-axis, the second partial winding generates a gradient $G_y$ in the y-axis, and the third partial winding generates a gradient $G_z$, in the z-axis. Each of these amplifiers has a digital-analog converter (DAC), controlled by a sequencer 18 for the accurately-times generation of gradient pulses.

A radio-frequency antenna 4 is located within the gradient field system 3, which converts the radio-frequency pulses provided by a radio-frequency power amplifier 24 into a magnetic alternating field for the excitation of the nuclei by tipping ("flipping") the spins in the subject or the region thereof to be examined, from the alignment produced by the basic magnetic field. The radio-frequency antenna 4 is composed of one or more RF transmitting coils and one or more RF receiving coils in the form of an annular, linear or matrix type configuration of coils. The alternating field based on the precessing nuclear spin, i.e. the nuclear spin echo signal normally produced from a pulse sequence composed of one or more radio-frequency pulses and one or more gradient pulses, is also converted by the RF receiving coils of the radio-frequency antenna 4 into a voltage (measurement signal), which is transmitted to a radio-frequency system 22 via an amplifier 7 of a radio-frequency receiver channel 8, 8'. The radio-frequency system 22 furthermore has a transmitting channel 9, in which the radio-frequency pulses for the excitation of the magnetic nuclear resonance are generated. For this purpose, the respective radio-frequency pulses are digitally depicted in the sequencer 18 as a series of complex numbers, based on a given pulse sequence provided by the system computer 20. This number series is sent via an input 12, in each case, as real and imaginary number components to a digital-analog converter (DAC) in the radio-frequency system 22 and from there to the transmitting channel 9. The pulse sequences are modulated in the transmitting channel 9 to a radio-frequency carrier signal, the base frequency of which corresponds to the resonance frequency of the nuclear spin in the measurement volume. The modulated pulse sequences of the RF transmitter coil are transmitted to the radio-frequency antenna 4 via the amplifier 24.

Switching from transmitting to receiving operation occurs via a transmission-receiving switch 6. The RF transmitting coil of the radio-frequency antenna 4 radiates the radio-frequency pulse for the excitation of the nuclear spin in the measurement volume M and scans the resulting echo signals via the RF receiving coils. The corresponding magnetic resonance signals obtained thereby are demodulated to an intermediate frequency in a phase sensitive manner in a first demodulator 8' of the receiving channel of the radio-frequency system 22, and digitalized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17. In an image processor 17, an MR image is reconstructed from the measurement data obtained in this manner through the use of the method according to the invention, which includes computation of at least one disturbance matrix and the inversion thereof, in the image processor 17. The management of the measurement data, the image data, and the control program occurs via the system computer 20. The sequencer 18 controls the generation of the desired pulse sequences and the corresponding scanning of k-space with control programs, in particular, in accordance with the method according to the invention. The sequencer 18 controls accurately-timed switching (activation) of the gradients, the transmission of the radio-frequency pulse with a defined phase amplitude, and the reception of the magnetic resonance signals. The time base for the radio-frequency system 22 and the sequencer 18 is provided by a synthesizer 19. The selection of appropriate control programs for the generation of an MR image, which are stored, for example, on a DVD 21, as well as other user inputs such as a desired number n of adjacent clusters, which are to collectively cover the desired k-space, and the display of the generated MR images, occurs via a terminal 13, which includes units for enabling input entries, such as, e.g. a keyboard 15, and/or a mouse 16, and a unit for enabling a display, such as, e.g. a display screen.

In FIG. 1, the components encompassed (built into) the basic field magnet 1, into which the patient 0 is moved, form a magnetic resonance scanner, which is operated by the multiple computers and processors that are also shown in FIG. 1. These computers and processors shown in FIG. 1 are programmed individually or collectively to execute the method according to the invention.

Calculation of ADC Maps

The inventive method and apparatus are described below using the example of calculating an ADC map in diffusion MRI.

It is necessary to introduce the equations of the relevant signal model in diffusion imaging. First, for all the acquisitions used to calculate the ADC map, all imaging parameters except the b-values, e.g. TR and TE, are kept the same so that common factors such as T1 and T2/T2* effects can be ignored in the signal model. For the n acquisitions with b-values that are not completely the same, the general equations of the acquired MR signal are given by $$S_1 = S_0 e^{-b_1 \cdot ADC} \quad [1]$$
$$\ldots$$
$$S_n = S_0 e^{-b_n \cdot ADC}$$

where $S_0$ is pixel intensity without diffusion weighting, i.e. corresponding to b=0.

Eq. [1] has two unknown variables, $S_0$ and ADC, which can be determined using acquisitions with different b-values equal to or greater than 2.

Log-Linear Fitting

The conventional method to solve for these unknown variables is the log-linear fitting method (LL). If the log of both sides of Eq. [1] is taken, and $$y_i = \log(S_i) \quad [2]$$

is defined, Eq. [1] is converted to $$y_1 = \log(S_0) - ADC \cdot b_1 \quad [3]$$
$$\ldots$$
$$y_n = \log(S_0) - ADC \cdot b_n$$

With further definitions $$x_i = b_i \quad [4]$$

$$\bar{y} = \frac{\sum_{i=1}^{n} y_i}{n} \quad [5]$$

$$\bar{x} = \frac{\sum_{i=1}^{n} x_i}{n} \quad [6]$$

ADC is calculated as $$ADC = \frac{n\bar{x}\bar{y} - \sum_{i=1}^{n} x_i y_i}{\sum_{i=1}^{n} x_i^2 - n\bar{x}^2} \quad [7]$$

In practice, one or more of the high b-value DW images can be measured multiple times and averaged, so that the averaged high b-value DW images can have sufficient SNR to perform log-linear fitting. However, the noise bias is independent of averaging, causing that this method suffers from a bias in the resultant ADC, because the source data of the high b-value DW images are contaminated by noise of non-zero expectation value (due to the common operation to get the magnitude of the original complex DW images), the averaged images still have systematic errors in the image intensity.

Least Squares Nonlinear Fitting

Another common technique to solve the unknown variables in non-linear equations is the least squares non-linear fitting method. In short, the least squares non-linear fitting method seeks to minimize Eq. [8]

$$E = \sum_{i=1}^{n} |S_i - F_i|^2 \quad [8]$$

Typically $$m_0(b_i) = S_0 e^{-b_i \cdot ADC} \quad [9]$$

$$F_i = m_0(b_i) \quad [10]$$

With at least two different b-values, there are various least squares non-linear fitting methods to solve this problem. For example, the Levenberg-Marquardt algorithm (Levenberg K. A method for the solution of certain non-linear problems in least squares. Q Appl Math 1944; 2:164-168), also known as the damped least-squares method, can be used.

Parameters Related to the Probability Density Function of Noise Distribution

Signal intensities in an MR image are corrupted by noise. In MRI data, which are naturally complex data, the noise distribution is known to obey a Gaussian or normal distribution (Constantinides C D, Atalar E, McVeigh E R. Signal-to-noise measurements in magnitude images from NMR phased arrays. Magn Reson Med 1997; 38:852-857. Erratum in Magn Reson Med 2004; 52:219).

In DWI, magnitude data are usually used in ADC calculation, i.e. $S_i$ is magnitude only without phase. This magnitude operation causes the noise distribution in the magnitude data to be changed to a Rician distribution, or more generally, non-central chi-squared distribution for multi-channel coils (Constantinides C D, Atalar E, McVeigh E R. Signal-to-noise measurements in magnitude images from NMR phased arrays. Magn Reson Med 1997; 38:852-857. Erratum in Magn Reson Med 2004; 52:219). As a result, signal intensities at low SNR have a systematic bias related to the noise, which appears as a value ($m_{bias}$) higher than the noise-free true value of the magnitude ($m_0$). If this effect is not properly accounted for, the estimates of the ADC will be biased.

In order to account for the noise effects in the magnitude data, the probability density function (PDF) of the non-central chi-squared distribution, given in Eq.[11], is utilized (Constantinides C D, Atalar E, McVeigh E R. Signal-to-noise measurements in magnitude images from NMR phased arrays. Magn Reson Med 1997; 38:852-857. Erratum in Magn Reson Med 2004; 52:219).

$$PDF(m) = \frac{m^L}{\sigma^2} m_0^{1-L} e^{-\frac{m_0^2 + m^2}{2\sigma^2}} I_{L-1}\left(\frac{mm_0}{\sigma^2}\right) \quad [11]$$

where m is the random variable corresponding to the reconstructed MR magnitude, L is the effective number of receiver channels (Constantinides C D, Atalar E, McVeigh E R. Signal-to-noise measurements in magnitude images from NMR phased arrays. Magn Reson Med 1997; 38:852-857. Erratum in Magn Reson Med 2004; 52:219 and Aja-Fernández S, Tristán-Vega A, Alberola-López C. Noise estimation in single- and multiple-coil magnetic resonance data based on statistical models. Magn Reson imaging 2009; 27:1397-1409), $m_0$ is the noise-free true magnitude whose value depends on the corresponding b-value as defined in Eq. [9], $\sigma^2$ is the noise variance of the normal distribution in the original complex MR data, and $I_{L-1}$ is the (L−1)th-order modified Bessel function of the first kind. Eq. [11] generalizes the non-central chi-squared distribution, and two special cases are worth noting. First, when there is only one single channel in the receiver (L=1), Eq. [11] simplifies to a Rician distribution. In addition, when the noise-free true magnitude $m_0$ equals zero, the PDF further simplifies to a Rayleigh distribution.

Based on the PDF of the non-central chi-squared distribution, several parameters that reflect the characteristics of the PDF can be calculated (Kristoffersen A. Optimal estimation of the diffusion coefficient from non-averaged and averaged noisy magnitude data. J Magn Reson 2007; 187: 293-305 and Walker-Samuel S, Orton M, McPhail L D, Robinson S P. Robust estimation of the apparent diffusion coefficient (ADC) in heterogeneous solid tumors. Magn Reson Med 2009; 62(2):420-429, and Veraart J, Rajan J, Peeters R R, Leemans A, Sunaert S, Sijbers J. Comprehensive framework for accurate diffusion MRI parameter estimation. Magn Reson Med 2013; 70:972-984).

One parameter is the maximum probability point, namely $m_{MP}$, which can be found by finding the m value corresponding to the maximum of the PDF curve using either analytic or numeric methods. $m_{MP}$ fulfills the equation below.

$$PDF(m_{MP}) = \max\{PDF(m)|_{m=0}^{\infty}\} \quad [12]$$

Another parameter is the median value, namely $m_{MD}$, which can be found by finding the m value corresponding to the 0.5 value of the cumulative distribution function (CDF) curve using either analytic or numeric methods. $m_{MD}$ fulfills the equation below.

$$CDF(m_{MD}) = \int_0^{m_{MD}} PDF(m)dm = 0.5 \quad [13]$$

And one other possible parameter is the expectation value, namely $m_{EX}$, which can be expressed in an analytic equation $$m_{EX} = {}_1F_1\left(-\frac{1}{2}, L, -\frac{m_0^2}{2\sigma^2}\right)\sigma\beta_L \quad [14]$$

where ${}_1F_1(\ldots)$ is the confluent hypergeometric function, $\beta_L$ is defined below $$\beta_L = \sqrt{\frac{\pi}{2}} \frac{(2L-1)!!}{2^{L-1}(L-1)!} \quad [15]$$

and ( ... )! and ( ... )!! are factorial and double factorial, respectively.

In the description of this invention, $m_{MP}$ is used as an example to demonstrate the inventive algorithm, but the algorithm can be extended to use the other parameters in a straightforward way.

Noise Variance Map

One other key parameter to consider is $\sigma^2$, the noise variance of the normal distribution in the original complex MR data. Equivalently important, the standard deviation $\sigma$, can be obtained if the noise variance is known.

There have been various methods to measure the noise in MR data, so that the noise characteristics such as SNR and noise variance can be calculated (Kellman P, McVeigh E R. Image reconstruction in SNR units: a general method for SNR measurement. Magn Reson Med 2005; 54:1439-1447, and Riffe M J, Blaimer M, Barkauskas K J, Duerk J L, Griswold M A. SNR estimation in fast dynamic imaging using bootstrapped statistics. Proc Intl Soc Mag Reson Med 15, 1879. 2007, and Robson P M, Grant A K, Madhuranthakam A J, Lattanzi R, Sodickson D K, McKenzie C A. Comprehensive quantification of signal-to-noise ratio and g-factor for image-based and k-space-based parallel imaging reconstructions. Magn Reson Med 2008; 60:895-907, and Wiens C N, Kisch S J, Willig-Onwuachi J D, McKenzie C A. Computationally rapid method of estimating signal-to-noise ratio for phased array image reconstructions. Magn Reson Med 2011; 66:1192-1197). Among them, a pragmatic and promising approach is to use the raw data of a single acquisition, and feed it through the image reconstruction multiple times, each time with a different noise realization added (Riffe M J, Blaimer M, Barkauskas K J, Duerk J L, Griswold M A. SNR estimation in fast dynamic imaging using bootstrapped statistics. Proc Intl Soc Mag Reson Med 15, 1879. 2007, and Robson P M, Grant A K, Madhuranthakam A J, Lattanzi R, Sodickson D K, McKenzie C A. Comprehensive quantification of signal-to-noise ratio and g-factor for image-based and k-space-based parallel imaging reconstructions. Magn Reson Med 2008; 60:895-907, and Wiens C N, Kisch S J, Willig-Onwuachi J D, McKenzie C A. Computationally rapid method of estimating signal-to-noise ratio for phased array image reconstructions. Magn Reson Med 2011; 66:1192-1197). This method has been proposed with use of natural noise (Riffe M J, Blaimer M, Barkauskas K J, Duerk J L, Griswold M A. SNR estimation in fast dynamic imaging using bootstrapped statistics. Proc Intl Soc Mag Reson Med 15, 1879. 2007), and synthetic noise (Robson P M, Grant A K, Madhuranthakam A J, Lattanzi R, Sodickson D K, McKenzie C A. Comprehensive quantification of signal-to-noise ratio and g-factor for image-based and k-space-based parallel imaging reconstructions. Magn Reson Med 2008; 60:895-907). The latter study introduced the term pseudo-replicas. The pseudo-replicas can then be used to derive the SNR or noise variance. This measure includes not only the basic noise physics of the patient and the hardware, but also the way the signal processing chain is dealing with the noise. As such, it is independent of the actual sequence, reconstruction, and post-processing implementation.

The noise variance map in accordance with the invention is accomplished by an extension of the pseudo-replicas approach, which is described in (Wiens C N, Kisch S J, Willig-Onwuachi J D, McKenzie C A. Computationally rapid method of estimating signal-to-noise ratio for phased array image reconstructions. Magn Reson Med 2011; 66:1192-1197).

Forward Approach to Calculate ADC

The inventive method takes all the above factors into consideration. The algorithm is described in detail in the flowchart shown in FIG. 2. In general, any iterative fitting algorithm can be used to drive the process. In the example of the invention shown in FIG. 2, the Levenberg-Marquardt fitting algorithm is used as an example.

As described in the flowchart, $m_0$ is first calculated using Eq. [9], and then $m_{MP}$ (or $m_{MD}$, $m_{EX}$) is calculated. This calculation order, i.e. calculating $m_0$ and then the corresponding $m_{MP}$ (or $m_{MD}$, $m_{EX}$) to be used in the fitting process, is referred to as the Forward Approach in this inventive method. The corresponding $m_{MP}$ (or $m_{MD}$, $m_{EX}$) are then used to replace the Fi in Eq. [8] for the fitting process to fit the parameters that are of interest to obtain the eventual values.

In practice, in order to improve the overall SNR and accuracy, one or more of the high b-value DW images can also be measured multiple times. The inventive method, however, does not average these measurements of the same b-values, unlike in the common methods. Instead, each measurement is treated independently during the fitting process, i.e. as one equation in Eq. [1]. This strategy assures that each measurement of the high b-value DW images can contribute independently and correctly to the estimation of the ADC. Averaging the measurements of the same b-values would be contrary to the basis of the inventive method.

In addition, the inventive method can be applied to calculate the ADC map for individual diffusion weighting direction, as well as the $ADC_{trace}$ map. For computation efficiency, the trace weighted images ($Trace_W$) can be calculated by taking the geometric average of the DW images in three orthogonal diffusion directions, as in Eq. [16], where $S_{(d)}$ represents the pixel intensity in the dth diffusion direction; and then the proposed method can be performed based on the $Trace_W$ images to fit the $ADC_{trace}$ map.

$$Trace_W = \sqrt[3]{S_{(1)}S_{(2)}S_{(3)}} \quad [16]$$

Example Preliminary Results

Figure 3:
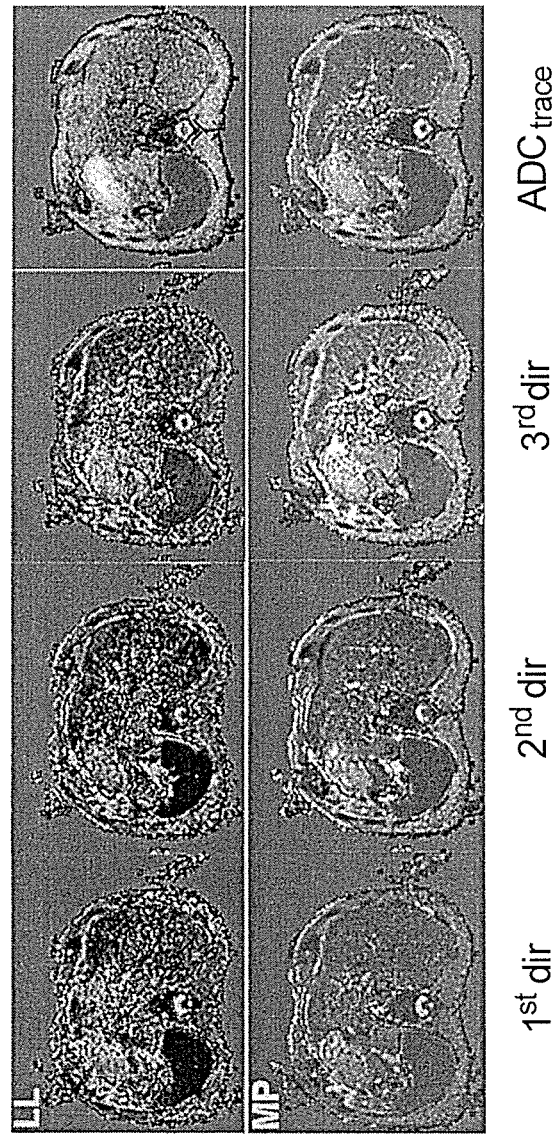
FIG. 3 shows examples of MR images generated according to the prior art, using only a log-linear algorithm, compared with images generated in accordance with the present invention.

Compared to the results of the commonly used LL algorithm, exemplary results of the inventive method are shown in FIG. 3 designated with MP, where $m_{MP}$ was used to account for the noise of high b-value images. It is noted that MP provides a more uniform, less noisy ADC map than the commonly used LL method for the example case shown here. Finer details such as vessels in the liver can be seen on the ADC maps generated using the MP method, but not on the ADC maps generated using the LL method. Quantitatively, MP can improve the robustness of ADC calculation (reduced std; smaller variation using results from most b-values as reference), especially in the liver region.

FIG. 3 show examples of resultant ADC maps for each diffusion weighting direction and the $ADC_{trace}$ map. The DW data were acquired with 3 diffusion weighting directions, with b=50, 400, 800, 1200, 2000, 400, 800, 1200, 2000, 800, 1200, 2000, 1200, 2000, 2000 s/mm² for each acquisition, respectively. The background shows the area that was either masked out as background air regions (outside the body), or the area where algorithms failed to generate an ADC value (inside the body).

Figure 2:
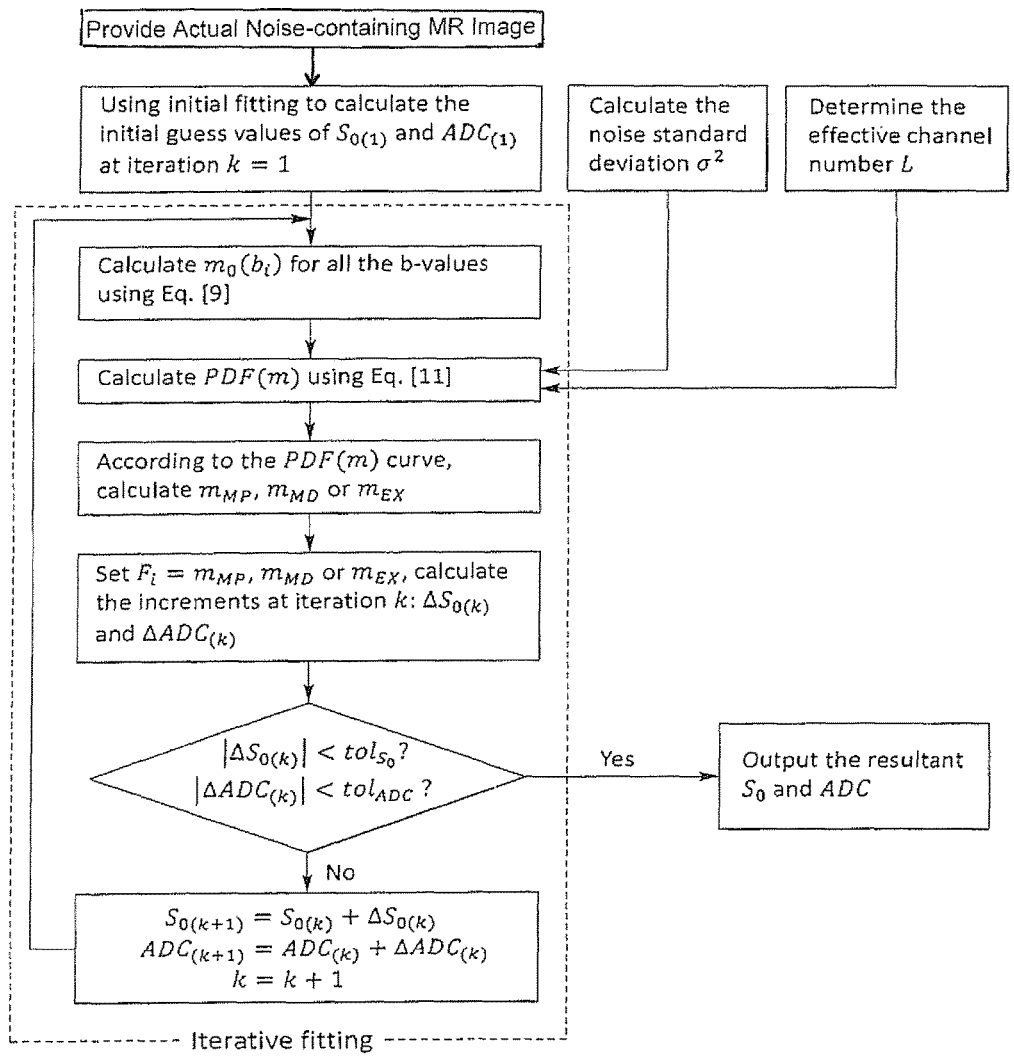
FIG. 2 is a flowchart that illustrates an exemplary embodiment of the method according to the invention.

Once the $S_0$ and ADC maps are calculated or fitted as described in the previous sections and in the flowchart in FIG. 2, synthetic diffusion weighted images $\hat{S}$ can be calculated using $$\hat{S}(b)=S_0 e^{-b \cdot ADC} \quad [17]$$

where b in the Eq. [17] can be any arbitrary values, not necessarily the actual b values that were acquired to calculate the ADC and $S_0$. For example, based on a diffusion weighted imaging acquisition with b values of 50, 400 and 800 s/mm², $S_0$ and ADC maps can be calculated, and then used to calculate synthetic diffusion weighted images $\hat{S}(b)$ corresponding to any b values, for example, b values that are not acquired such as 2000 or 3000 s/mm², or b values that are acquired such as 50, 400 and 800 s/mm². Because the ADC and $S_0$ maps are corrected for noise bias, the synthetic diffusion weighted images, compared to the diffusion weighted images S(b) that are actually acquired with the same b values, have reduced noise and improved SNR, and are better to appreciate, which is one advantage of the synthetic diffusion weighted images. And another advantage of synthetic diffusion weighted images is that they can provide images corresponding to any arbitrary b values without the need to actually acquire the images.

Calculation of T2, R2, T2* or R2* Maps

The inventive method and apparatus can be extended to calculate T2, R2, T2* or R2* maps in spin echo (SE), turbo/fast spin echo (TSE/FSE) or gradient echo (GRE) MRI, respectively. For the R2 calculation, the signal intensity typically is measured with a SE or TSE sequence. In contrast, for the R2* calculation, the signal intensity typically is measured with a GRE sequence. The equations and descriptions in this section use the example of calculating the R2 map, but they actually apply to both R2 and R2*, because their signal model equations have the same form.

For all the acquisitions used to calculate the R2 map, all imaging parameters except the TE values, e.g. TR and flip angle, are kept the same so that common factors such as T1 effects can be ignored in the signal model. For the n acquisitions with TE values that are not completely the same, the general equations of the acquired MR signal are given by $$S_1 = S_0 e^{-TE_1 \cdot R2} \quad [18]$$

$$\ldots$$

$$S_n = S_0 e^{-TE_n \cdot R2}$$

where S0 is pixel intensity corresponding to TE=0. The two unknown variables, $S_0$ and R2, can be determined using acquisitions with different TE values equal to or greater than 2.

Similarly, in order to get the results of the LL fitting, take log of both sides of Eq. [18] with the definition in Eq. [2], Eq. [18] is converted to $$y_1 = \log(S_0) - R2 \cdot TE_1 \quad [19]$$

$$\ldots$$

$$y_n = \log(S_0) - R2 \cdot TE_n$$

with definitions in Eq. [5] and [6], and further definition of $$x_i = TE_i \quad [20]$$

R2 can be calculated using the LL method as $$R2 = \frac{n\bar{x}\bar{y} - \sum_{i=1}^{n} x_i y_i}{\sum_{i=1}^{n} x_i^2 - n\bar{x}^2} \quad [21]$$

To obtain the R2 results using the inventive algorithm, Eqs. [8]-[15] are still suitable except that Eq. [9] shall be replaced with $$m_0(TE_i) = S_0 e^{-TE_i \cdot R2} \quad [22]$$

After R2 or R2* values are obtained, the corresponding T2 and T2* values can be easily obtained by $$T2 = 1/R2 \quad [23]$$

$$T2^* = 1/R2^* \quad [24]$$

Calculation of Proton Density Fat Fraction, Proton Density Water Fraction, T2*/R2* or T2/R2 Maps The inventive method and apparatus can be extended to calculate proton density fat fraction (PDFF), proton density water fraction (PDWF), T2, R2, T2* or R2* maps in SE, TSE/FSE or GRE MRI, respectively. For the R2 calculation, the signal intensity typically is measured with a SE or TSE sequence. In contrast, for the R2* calculation, the signal intensity typically is measured with a GRE sequence. Both sequences can generate the PDFF and PDWF maps. The equations and descriptions in this section use the example of calculating the R2* map, but they actually apply to both R2 and R2*, because their signal model equations have the same form.

The extension of the inventive method and apparatus in this section is related to previous art (Zhong X, Nickel M D, Kannengiesser S A R, Dale B M, Kiefer B, Bashir M R. Liver fat quantification using a multi-step adaptive fitting approach with multi-echo GRE imaging. Magn Reson Med 2014; 72:1353-1365, and Zhong X, Nickel M D, Kannengiesser S A R. MR fat and iron quantification using a multi-step adaptive fitting approach with multi-echo magnetic resonance imaging. US patent US20140126795 A1, 2014). And the description in this section is based on the assumption that water and fat have the same T2*/R2* value (effective T2*/R2*), to emphasize the concept of this invention. The same concept can also be extended to the more general scenarios where the T2*/R2* values of water and fat shall be considered differently (Zhong X, Nickel M D, Kannengiesser S A R, Dale B M, Kiefer B, Bashir M R. Liver fat quantification using a multi-step adaptive fitting approach with multi-echo GRE imaging. Magn Reson Med 2014; 72:1353-1365, and Zhong X, Nickel M D, Kannengiesser S A R. MR fat and iron quantification using a multi-step adaptive fitting approach with multi-echo magnetic resonance imaging. US patent US20140126795 A1, 2014).

In an embodiment, sufficiently low flip angles are utilized in the data acquisition, so that $T_1$ effects can be neglected. All imaging parameters except the TE values, e.g. TR and flip angle, are kept the same. For the n acquisitions with TE values that are not completely the same, at the n-th echo time ($TE_n$), the general equation of the acquired MR signal is modeled by $$|S_n| = |(M_w + c_n M_f) \cdot e^{-R2^* * TE_n}| \quad [25]$$

In this equation, there are three unknown values to fit: $M_w$ and $M_f$ are the water and fat signal magnitudes, respectively, which are proportional to the magnetization or proton density of those tissue types; and R2* is the transverse relaxation rate of the water and fat mixture (assuming water and fat have the same R2*).

$c_n$ is the complex coefficient at $TE_n$ due to the difference of fat and water in the spectrum, and can be calculated based on the specific fat content in the body region of interest. In an embodiment, the complex coefficient $c_n$ can be calculated as $$c_n = \sum_{i=1}^{m} w_i e^{j(2\pi \Delta f_i TE_n)} \quad [26]$$

where m is the number of the fat spectral peaks in the model, $w_i$ and $\Delta f_i$ are the fat peak weighting factors and the resonance frequency offsets relative to the water peak on the spectrum. In another embodiment, one can calculate $c_n$ based on the time-domain calibration of fat signal dephasing using the free induction decay signal from a multiple echo single-voxel spectroscopy measurement using stimulated echo acquisition mode (STEAM) (Nickel M D, Kannengiesser S A R, Dale B M, Kiefer B. Time-domain calibration of fat signal dephasing from multi-echo STEAM spectroscopy for multi-gradient-echo imaging based fat quantification. The 23rd Proc. Intl. Soc. Mag. Reson. Med. 2015; 3658).

Correspondingly, Eqs. [8] and [9] shall be modified as $$E = \Sigma_{i=1}^{n} \||S_i| - |F_i|\|^2 \quad [27]$$

and $$m_0(TE_i) = (M_w + c_n M_f) \cdot e^{-R2^* * TE_n} \quad [28]$$

And then the similar workflow can be applied to fit the $M_w$, $M_f$ and R2* with the noise bias accounted. The PDFF and PDWF can be then calculated as $$PDFF = \frac{M_f}{M_w + M_f} \quad [29]$$

$$PDWF = \frac{M_w}{M_w + M_f} \quad [30]$$

Calculation of T1 Maps

The inventive method and apparatus can be extended to calculate T1 maps in SE or TSE/FSE MRI. In an embodiment used as an example in this section, to measure the longitudinal relaxation time T1 of each sample, an inversion recovery (IR) TSE sequence is obtain images at different inversion times (TI). The signal equation for each $TI_n$, is given by $$S_n = K(1 - 2e^{-TI_n/T1} + e^{-TR/T1}) \quad [31]$$

where K is the signal intensity in the absence of $T_1$ weighting. K and TI are the unknown values to fit in the fitting process.

To obtain the T1 results using the inventive algorithm, Eqs. [8]-[15] are still suitable except that Eq. [9] shall be replaced with $$m_0(TI_i) = K(1 - 2e^{-TI_i/T1} + e^{-TR/T1}) \quad [32]$$

And then the similar workflow can be applied to fit the K and T1 with the noise bias accounted.

An Alternative Approach to Convert the Signal with Noise Bias Effects to the Corrected Signal Free of Noise Bias Effects (Backward Approach)

In addition to the Forward Approach mentioned in the previous sections, this invention method also encompass a Backward or Inverse Approach.

As described in the Forward Approach, typically the mapping of the theoretical unbiased value $m_0$ to the noise-biased value ($m_{MP}$, $m_{MD}$ or $m_{EX}$) is analytically known. However, the analytical equations or solutions in the Forward Approach are computationally expensive, and because they may need to be computed for many times in the iterative fitting algorithm, it could lead to an inefficient evaluation. Alternatively, an efficient evaluation may be achieved by performing a Backward or Inverse Approach, which provides an equivalent way to solve this problem by mapping the noise-biased value ($m_{MP}$, $m_{MD}$ or $m_{EX}$) back to the theoretical unbiased value $m_0$. Details of the Backward/Inverse Approach are described below.

In the Forward Approach, given the unbiased value $m_0$ and the noise standard deviation a, the noise-biased value ($m_{MP}$, $m_{MD}$ or $m_{EX}$) can be calculated and determined using the algorithms described by Eq. [13]-[15].

Mapping inversely, i.e. from the noise-biased value ($m_{MP}$, $m_{MD}$ or $m_{EX}$) back to the theoretical unbiased value $m_0$, is achieved through in these steps:

First, the noise-biased value is divided by the estimated noise standard deviation value, i.e. normalize the noise-biased value (equivalent to that the noise is equal to unit one). Correspondingly, the noise-biased values are normalized in the same way.

$$m'_0 = \frac{m_0}{\sigma} \quad [33]$$

$$m'_{MP} = \frac{m_{MP}}{\sigma} \quad [34]$$

$$m'_{MD} = \frac{m_{MD}}{\sigma} \quad [35]$$

$$m'_{EX} = \frac{m_{EX}}{\sigma} \quad [36]$$

Second, since the inverse function equations of the Eq. [13]-[15] may not be known or described analytically to map the noise-biased value ($m_{MP}$, $m_{MD}$ or $m_{EX}$) back to the theoretical unbiased value $m_0$, practically, it can be modelled e.g. by a lookup table or a stepwise polynomial approximation such as the Chebychev approximation. Those allow an efficient evaluation with a selectable precision to map $m'_{MP}$, $m'_{MD}$ or $m'_{EX}$ to $m'_0$.

$$m'_{MP}, m'_{MD} \text{ or } m'_{EX} \xrightarrow{\text{Look up table}} m'_0 \quad [37]$$

$$m'_{MP}, m'_{MD} \text{ or } m'_{EX} \xrightarrow{\text{stepwise polynomial approximation}} m'_0 \quad [38]$$

Lastly, the theoretical unbiased value $m_0$ can then be obtained in the original unit by multiplying $m'_0$ with the noise value.

$$m_0 = m'_0 \cdot \sigma \quad [39]$$

With the above steps, the acquired image intensity values with noise bias effects can be converted or mapped to the corrected image intensity values that are free of noise bias effects. Regular fitting methods such as LL (log log) and LS (least squares) can then be applied to the corrected image intensity values that are free of noise bias effects to fit the parameters of interest.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to correct noise effects in parameter fitting using magnetic resonance (MR) images, comprising:

in a processor, executing a fitting algorithm to calculate initial values for each of selected variables in a signal model that models noise effects in a modeled, noise-containing MR image;

in said processor, executing an iterative fitting algorithm, that is the same or a different fitting algorithm, to generate final values for each of said selected variables;

providing said processor with an actual MR image that contains noise and, in said processor, using said final values of said selected variables to correct effects of said noise in said actual MR image by executing a calculation algorithm selected from the group consisting of a forward calculation algorithm and a backward/inverse calculation algorithm, thereby producing a parameter mapping image with no noise bias effects or errors when either said forward calculation algorithm or said backward/inverse algorithm is used; and making the parameter mapping image with no noise bias effects or errors, available in electronic form at an output of said processor, as a data file.

2. A method as claimed in claim 1 wherein said modeled, noise-containing MR image is a model diffusion-weighted MR image, and wherein said actual MR image is an acquired diffusion-weighted MR image, and wherein one of said selected variables is an apparent diffusion coefficient (ADC).

3. A method as claimed in claim 2 comprising, in said processor, using said final value of said ADC to generate an ADC map and a S0 map, and applying said ADC map and S0 map to calculate a synthetic diffusion-weighted MR image pixel-by-pixel with no noise bias effects or errors.

4. A method as claimed in claim 2 comprising executing each iteration of said iterative fitting algorithm independently for each of a plurality of acquired diffusion-weighted MR images, which were acquired with respectively different b-values.

5. A method as claimed in claim 1 comprising iteratively executing a Levenberg-Marquardt fitting algorithm as said iterative fitting algorithm.

6. A method as claimed in claim 1 comprising, when using said backward/inverse calculation algorithm, also producing an image corresponding to a predetermined initial condition, and also making said image corresponding to said predetermined initial condition available in electronic form at an output of said processor as a data file.

7. A method as claimed in claim 6 wherein said modeled, noise-containing MR image is a model diffusion-weighted MR image, and wherein said predetermined initial condition is a b value equal to 0.

8. A magnetic resonance (MR) apparatus, comprising:
an MR scanner;
a control computer configured to operate said MR scanner, while a subject is situated therein, to acquire an actual MR image of the subject, which contains noise;
a processor configured to execute a fitting algorithm to calculate initial values for each of selected variables in a signal model that models a noise effect in a modeled, noise-containing MR image;
said processor being configured to execute an iterative fitting algorithm, that is the same or a different fitting algorithm, to generate final values for each of said selected variables;
said processor being provided with said actual MR image that contains noise, and said processor being configured to use said final values of said selected variables to correct effects of said noise in said actual MR image by executing a calculation algorithm selected from the group consisting of a forward calculation algorithm and a backward/inverse calculation algorithm, thereby producing a parameter mapping image with no noise bias effects or errors when either said forward calculation algorithm or said backward/inverse calculation algorithm is used; and
said processor being configured to make the parameter mapping image with no noise bias effects or errors available in electronic form at an output of said processor, as a data file.

9. An apparatus as claimed in claim 8 wherein said modeled, noise-containing MR image is a model diffusion-weighted MR image, and wherein said control computer is configured to acquire said actual MR image as an acquired diffusion-weighted MR image, and wherein one of said selected variables are an apparent diffusion coefficient (ADC).

10. An apparatus as claimed in claim 9 wherein said processor is configured to use said final value of said ADC to generate an ADC map and a S0 map, and to apply said ADC map and S0 map to calculate a synthetic diffusion-weighted MR image pixel-by-pixel with no noise bias effects or errors.

11. An apparatus as claimed in claim 9 wherein said processor is configured to execute each iteration of said iterative fitting algorithm independently for each of a plurality of acquired diffusion-weighted MR images, which were acquired with respectively different b-values.

12. An apparatus as claimed in claim 8 wherein said processor is configured to iteratively execute a Levenberg-Marquardt fitting algorithm as said iterative fitting algorithm.

13. An apparatus as claimed in claim 8 wherein said processor is configured, when using said backward/inverse calculation algorithm, to also produce an image corresponding to a predetermined initial condition, and also to make said image corresponding to said predetermined initial condition available in electronic form at an output of said processor as a data file.

14. An apparatus as claimed in claim 13 wherein said modeled, noise-containing MR image is a model diffusion-weighted MR image, and wherein said predetermined initial condition is a b value equal to 0.

15. A non-transitory, computer-readable data storage medium encoded with programming instructions, said storage medium being loaded into a computer and said programming instructions causing said computer to:
execute a fitting algorithm to calculate initial values for each of selected variable in a signal model that models a noise effect in a model, noise-containing MR image;
execute an iterative fitting algorithm, that is the same or a different fitting algorithm, to generate final values for each of said selected variables;
receive an actual MR image that contains noise, and use said final values of said selected variables to correct effects of said noise in said actual MR image by executing a calculation algorithm selected from the group consisting of a forward calculation algorithm and a backward/inverse calculation algorithm, thereby producing a parameter mapping image with no noise bias effects or errors when either said forward calculation algorithm or said backward/inverse calculation algorithm is used; and
make one of the parameter mapping image with no noise bias effects or errors available in electronic form at an output of said computer, as a data file.

16. A non-transitory, computer-readable data storage medium as claimed in claim 15 wherein said programming instructions further cause said computer to, when using said backward/inverse calculation algorithm, also produce an image corresponding to a predetermined initial condition, and also make said image corresponding to said predetermined initial condition available in electronic form at an output of said processor as a data file.

17. A non-transitory, computer-readable data storage medium as claimed in claim 16 wherein said modeled, noise-containing MR image is a model diffusion-weighted MR image, and wherein said programming instructions further cause said computer to use, as said predetermined initial condition, a b value equal to 0.

* * * * *